United States Patent [19]

Roberts

[11] Patent Number: 5,077,045
[45] Date of Patent: Dec. 31, 1991

[54] **METHOD FOR SUPPRESSING WEED GRASSES USING *XANTHOMONAS CAMPESTRIS***

[75] Inventor: David L. Roberts, East Lansing, Mich.

[73] Assignee: Michigan State University, East Lansing, Mich.

[21] Appl. No.: 897,356

[22] Filed: Aug. 16, 1986

[51] Int. Cl.$^5$ .................. A01N 63/00; C12N 1/20; C12R 1/64
[52] U.S. Cl. .................. 424/93; 435/252.1; 435/910; 71/65
[58] Field of Search .................. 71/65, 79; 435/260, 435/910, 253, 252.1; 424/93

[56] References Cited

U.S. PATENT DOCUMENTS

| | | | |
|---|---|---|---|
| 4,226,940 | 8/1980 | Storrs | 435/260 |
| 4,606,751 | 8/1986 | Van Dyke et al. | 71/79 |
| 4,672,037 | 6/1987 | Daggett et al. | 435/253 |
| 4,753,670 | 6/1988 | Leth | 71/79 |
| 4,755,208 | 7/1988 | Riley et al. | 71/79 |

OTHER PUBLICATIONS

Egli, T. and D. Schmidt, "Pathogenic Variation Among the Causal Agents of Bacterial Wilt of Forage Grasses", *Phytopath. Z.*, 104(1982), pp. 137–150.
Bradbury, J. F., "Xanthomonas", in Krieg, N. *Bergey's Manual of Systematic Bacteriology* (Baltimore, MD, Williams & Wilkins, 1984), pp. 199–210.
Roberts, D. L. et al., Plant Disease 65, 1014–1015 (1981).
Roberts et al., Plant Disease 66, 804–806 (1982).
Roberts, et al., Scanning Electron Microscopy IV, 1719–1722, (1983).
Roberts, D. L., Phytopathology 73, 810 (1984)/and Phytopathology 74, 813 (1984).
Roberts, D. L., Phytopathology 75, 1289 (1985).
Egli T., et al.,Phytopath Z. 82, 111–121 (1975).
Wilkins, et al., Plant Path 26, 99 (1977).
DeCleene, et al., Parasitica, 37 (1), 29–34 (1981).
Leyns, et al., Parasitica 37, 131–133 (1981).
Van Den Mooter, et al., Med. Fac. Landbouww Rijksuniv. Gent. 46/3, 787–792 (1981).
Van Den Mooter, et al., Parasitica 37 (1): 23–28 (1981).
Proc. Fifth Int. Conf. Path Bact., Calif. 332–333 (1981).
Egli, T., et al., Phytopath Z. 104, 138–150 (1982).
Leyns et al, Med Fac. Landbouww Rijksuniv Gent. 47/3, 1079–1081 (1982).

*Primary Examiner*—Howard J. Locker
*Assistant Examiner*—Charles L. Patterson, Jr.
*Attorney, Agent, or Firm*—Ian C. McLeod

[57] ABSTRACT

A method for controlling weed grasses using a bacterium which is a *Xanthomonas campestris* pathovar which produces a wilt in the weed grass is described. In particular the use of a *Xanthomonas campestris* which infects *Poa annua* types to suppress or kill this weed grass is described. The method allows non-weed grasses to develop without interference from weed grasses to improve lawns, golf courses and the like.

14 Claims, No Drawings

METHOD FOR SUPPRESSING WEED GRASSES USING *XANTHOMONAS CAMPESTRIS*

BACKGROUND OF THE INVENTION

(1) Summary

The present invention relates to a method for controlling weed grasses by infecting them with a *Xanthomonas campestris* pathovar which does not infect non-weed grasses. In particular the present invention relates to the use of *Xanthomonas campestris* NRRL-B-18078 to suppress or kill the weed grasses.

(2) Prior Art

Bacteria infect grasses causing the grasses to be suppressed or killed. These infections have been known in other parts of the world as important problems for the maintenance of desirable grasses. So far as the inventor is aware, the present invention is the first attempt to suppress or kill a weed grass by applying a weed suppressing pathovar of bacteria to the grass. This method of biological control eliminates the need for herbicides which are relatively toxic chemicals to people and the environment.

A bacterial infection of Toronto creeping bentgrass which is used on golf putting greens is described by Roberts, D. L., et al in Plant Disease 65, 1014-1015 (1981); Roberts, D. L., et al, Plant Disease 66, 804-806 (1982); Roberts, D. L., et al, Scanning Electron Microscopy IV, 1719-1722 (1983). The bacterium was identified as a *Xanthomonas campestris* by Roberts, D. L. in Phytopathology 73, 810 and 74, 813 (1984). The solution to the problem was treatment of the infection with oxytetracycline, an antibiotic. A disease of *Poa annua* L. was also described by Roberts, D. L. In Phytopathology 75 1289 (1985).

The diseases caused by *Xanthomonas campestris* pathovars has also been studied by others and has been found to be selectively pathogenic to particular grass species. Egli T., et al Phytopath Z. 82, 111-121 (1975) first characterized a bacterial infection of cut grasses. Other publications include: Wilkins, P. W., et al, Plant Path 26, 99 (1977); DeCleene, M., et al., Parasitica 37(1) 29-34 (1981); Leyns, F., et al., Parasitica 37, 131-133 (1981); Van Den Mooter, M. et al, Med Fac Landbouww Rijksuniv. Gent 46/3, 787-792 (1981); Van Den Mooter, M., et al Parasitica 37 (1):23-28 (1981); Proc. Fifth Int. Conf. Path Bact, Calif 332-333 (1981); Egli, T. et al. Phytopath Z. 104, 138-150 (1982); and Leyns et al Med. Fac. Landbouww Rijksuniv Gent. 47/3 1079-1081 (1982).

Objects

It is therefore an object of the present invention to provide a method and compositions for biological control of weed grasses using a *Xanthomonas campestris* pathovar which selectively infects and suppresses or kills the weed grasses by causing a wilt disease. Further it is an object of the present invention to provide a method which is economical and eliminates the risk from non-toxic chemicals. These and other objects will become increasingly apparent by reference to the following description.

General Description

The present invention relates to a method for controlling a growing weed grass which comprises applying an infective amount of a *Xanthomonas campestris* pathovar to the weed grass whereby the weed grass is selectively suppressed or killed without suppressing or killing the non-weed grasses. A "weed" is a grass which is undesirable in a particular plot of grasses.

The present invention also relates to a bacterial concentrate which comprises: a *Xanthomonas campestris* pathovar specific for Poa annua having the identifying fermentation characteristics of NRRL-B-18078 which selectively infects and suppresses or kills *Poa annua*; and a preservation agent which may be used to preserve the viability of the strain upon storage.

Finally the present invention relates to the storage of a stable and biologically pure culture of a *Xanthomonas campestris* pathovar having the identifying fermentation characteristics of NRRL-B-18078 and which infects and suppresses or kills *Poa annua*.

The preferred strain of *Xanthomonas campestris* is deposited at the Northern Regional Research Laboratory in Peoria, Ill., as *Xanthomonas campestris* NRRL-B-18078. It is freely available to those who request it by name and number. Other *Xanthomonas campestris* which are pathovars for *Poa annua* and other weed grasses are easily isolated by those skilled in the art from infected grasses. *Xanthomonas campestris* pathovars cause wilt in other grasses such as Toronto bent grass (*Agrostis palustris*) which can be regarded as a weed in certain plots. The pathovars or strains of *Xanthomonas campestris* which cause diseases in grasses are discussed extensively in Phytopath. Z 104, 138-150 (1982). The method of the present invention can be used in plots where these grasses could be regarded as weeds.

The *Xanthomonas campestris* can be applied as an aqueous solution or on an inert carrier. The solution or carrier preferably contains between about $10^3$ and $10^8$ cells per gram (or ml for a solution); for reasons of economics and certainly of infection. It will be appreciated that larger or smaller numbers of the cells per gram or ml can be used so long as infection and suppression of the weed grass is achieved.

Preferably the *Xanthomonas campestris* are provided for shipment to users in the form of a concentrate containing at least about $10^6$ cells per gram or ml usually about $10^{14}$ per ml which can be lyophilized to a greater concentration mixed with a preservative agent, the exact composition of which depends upon the method of the preservation. The cells can be frozen or lyophilized. Where the cells are frozen glycerol or various sugars and fresh growth media can be used as preservation agents. Amounts usually between 5 and 50% by volume of the glycerol or sugars can be used. Where the cells are lyophilized, nutrient media and/or milk solids can be used for preservation. Generally the *Xanthomonas campestris* cells are grown to about $10^9$ cells per ml and may then be centrifuged or otherwise concentrated by removal of growth media. They can then be frozen or lyophilized. The lyophilized bacteria can be mixed with an inorganic solid carrier such as clays, talc, inert organic material or the like which may be dusted on the grasses or mixed with water and sprayed on the grasses.

The *Xanthomonas campestris* pathovars can also be applied using dried infected grass where the grass is used as a nutrient medium to grow and store the bacteria. All of these variations for storing, growing and applying the *Xanthomonas campestris* cultures will be obvious to those skilled in the art.

Generally a biologically pure culture of the *Xanthomonas campestris* is used for the application to the weed grass. There is no reason to have other bacteria competing to infect the plant, particularly other *Xanthomonas campestris* which do not suppress or kill the weed grass and which might infect non-weed grasses.

Specific Description

EXAMPLE 1

In this experiment a frozen culture of *Xanthomonas campestris* pathovar NRRL-B-18078 was used. The *Xanthomonas campestris* was isolated from annual bluegrasses in Pennsylvania and Michigan. The *Xanthomonas campestris* culture had been grown in nutrient broth, centrifuged and mixed with equal volumes of glycerol and nutrient medium before freezing The nutrient medium was Nutrient Broth (Difco Corp., Detroit, Mich.). The thawed culture was inoculated into nutrient medium, grown to about $10^{10}$ colony forming units (cfu) per ml, centrifuged and then re-suspended in tap water at a concentration of about $10^6$ cfu (colony forming units) per ml.

Three (3) pots of annual bluegrass (*Poa annua* and three (3) pots of perennial bluegrass (*Poa annua* var. *reptans*) were sprayed with the aqueous solution of the *Xanthomonas campestris* at about $10^6$ cfu/ml. Both grasses are weeds. The plants were trimmed to about one inch in height before spraying to insure infection. Each pot was sprayed with about 10 ml of solution. Two annual and two perennial grass pots were inoculated and one each served as a control.

After inoculation, each plant was then wrapped in a plastic bag with water in the bottom to maintain the relative humidity at 95 to 100% for about 48 hours to insure infection. The plants were then removed from the plastic bag and subjected to high intensity light (artificial sunlight) at 28° to 30° C.

Symptoms of wilt appeared in about seven (7) to ten (10) days. In the annual bluegrass sprayed with *Xanthomonas campestris* the leaf tips began to wilt, turn down and exhibited a bluegreen color. One (1) week later 30% of the annual bluegrass had wilted. In three (3) weeks 60 to 70% of the annual grasses were dead. The perennial type of annual bluegrass was also suppressed but at a slower rate. The uninoculated controls were unaffected.

As can be seen from the foregoing Example 1, *Xanthomonas campestris* NRRL-B-18078 over time killed the weed bluegrass. In mixed plots this allows non-weed grasses to replace the bluegrass and retard re-growth of the weed bluegrass. This result can be achieved when grasses on a golf course are sprayed in the manner of Example 1. Preferably the spraying is done under conditions of high humidity just after cutting to insure infection by the *Xanthomonas campestris.*

Thus the present invention provides a means for controlling weed grasses. This is particularly important in lawns and fairways and greens on golf courses to remove infestations of weed grasses.

It is intended that the foregoing Example be only illustrative and that the present invention be limited only by the hereinafter appended claims.

I claim:

1. A method for controlling growing annual and perennial *Poa annua* growing with a non-weed grass which comprises applying an infective amount of a *Xanthomonas campestris* pathovar having the identifying fermentation characteristics of NRRL-B-18078 to the *Poa annua* and the non-weed grass whereby the *Pao annua* is suppressed or killed without suppressing or killing the non-weed grass and wherein the non-weed grass replaces the *Poa annua*.

2. The method of claim 1 wherein the *Xanthomonas campestris* pathovar is deposited as NRRL-B-18078.

3. The method of claim 1 wherein an aqueous solution of the *Xanthomonas campestris* pathover containing between about $10^3$ and $10^8$ cells per ml is applied to the grass.

4. The method of claim 1 wherein the *Poa annua* is the annual type.

5. The method of claim 4 wherein the *Poa annua* is the perennial type.

6. A bacterial concentrate which comprises:
   (a) a *Xanthomonas campestris* pathovar for *Poa annua* having the identifying fermentation characteristics of NRRL-B-18078 which selectively infects and suppresses or kills the *Poa annua*; and
   (b) a preservation agent which preserves the viability of the strain upon storage.

7. The concentrate of claim 6 wherein the stabilizing agent is glycerol in an amount between about 5 and 50 percent by volume of the concentrate and wherein the concentrate is refrigerated or frozen.

8. The concentrate of claim 6 wherein the stabilizing agent is a nutrient medium for the *Xanthomonas campestris* and the concentrate is lyophilized.

9. The concentrate of claim 6 dried in diseased grass in which the specific *Xanthomonas campestris* pathovar has been grown.

10. The concentrate of claim 6 wherein the *Xanthomonas campestris* is mixed with an inert solid carrier for applying the bacterial culture to the grass.

11. A biologically pure culture of a *Xanthomonas campestris* pathovar having the identifying fermentation characteristics of NRRL-B-18078 and which infects and suppresses or kills *Poa annua* type grasses.

12. The culture of claim 11 containing at least about $10^6$ cells per ml.

13. The culture of claim 11 wherein the *Xanthomonas campestris* pathovar is *Xanthomonas campestris* pathovar NRRL-B-18078.

14. The culture of claim 11 containing between $10^6$ and $10^{14}$ cells per ml which is lyophilized.

* * * * *